US00PP11357P

United States Patent [19]

Kordes

[11] Patent Number: Plant 11,357

[45] Date of Patent: Apr. 18, 2000

[54] FLORIBUNDA ROSE PLANT NAMED 'KORAMVIS'

[75] Inventor: Wilhelm Kordes, Sparrieshoop, Germany

[73] Assignee: Bear Creek Gardens, Inc., Medford, Oreg.

[21] Appl. No.: 09/139,534

[22] Filed: Aug. 25, 1998

[51] Int. Cl.[7] ..... A01H 5/00

[52] U.S. Cl. ..... Plt./145

[58] Field of Search ..... Plt./144, 145, 134

*Primary Examiner*—Howard J. Locker

*Attorney, Agent, or Firm*—Klarquist Sparkman Campbell Leigh & Whinston, LLP

[57] ABSTRACT

Floribunda rose plant having yellow flower color; high flower production excellent vase life; good shipping qualities; and very vigorous growth habit.

1 Drawing Sheet

The present invention relates to a new and distinct variety of rose plant of the floribunda class which was discovered as a single branch spontaneous flower color mutation on a rose plant of the variety 'KORmiller' (U.S. Plant patent application Ser. No. 08/985,371, filed Dec. 4, 1997) growing in a greenhouse in Sparrieshoop, Germany, which bore a yellow flower as compared to the pastel pink flowers of 'KORmiller'. 'KORamvis' differs from its parent, 'KORmiller', principally in flower and peduncle color. It has the same growth, high flower production in a greenhouse, excellent shipping qualities of cut flowers, vase life and response to the environment as 'KORmiller'. Asexual reproduction of this new variety by budding, as performed at Sparrieshoop, Germany, and Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage: Spontaneous mutant of 'KORmiller' (U.S. Plant patent application Ser. No. 08/985,371, filed Dec. 4, 1997).

Classification:

*Botanical.*—*Rosa hybrida.*

*Commercial.*—Floribunda.

FLOWER

Observations made from specimens grown in a greenhouse environment at Somis, Calif., January 1997 to August 1998, and in Sparrieshoop, Germany.

Blooming habit: Continuous.

Bud:

*Size.* —About 1½ inches long when the petals start to unfurl.

*Form.*—Long, pointed ovoid, but somewhat blunt at the tip.

*Color.*—When sepals first divide, bud color is Yellow Group 11C. When half blown, the upper sides of the petals are Yellow Group 11C on the outer petals, changing to Yellow Group 11A in the center of the flower, and the lower sides of the petals are Yellow Group 11C on the outer petals changing to Yellow Group 11A in the center of the flower.

*Sepals.*—Color: Green Group 138B. Surface texture: Covered in fine hairs. There are three normally appendaged sepals. There are two unappendaged sepals with hairy edges.

*Receptacles.*—Color: Yellow-Green Group 146C. Shape: Funnel. Size: Medium (about 5/16 inch×¼ inch). Surface: Smooth.

*Peduncle.*—Length: Short, averaging about 2½ inches. Surface: Smooth. Color: Yellow-Green Group 146C. Strength: Stiff, erect.

Bloom:

*Size.*—Medium. Average open diameter is about 3½ inches.

*Borne.*—Singly.

*Stems.*—Strong, averaging about 18–22 inches in length.

*Form.*—When first open: High centered. Permanence: Retains its form to the end, outer petals edges curl slightly.

*Petalage.*—Number of petals under normal conditions: 25 to 30.

*Color.*—The upper sides of the petals are Yellow Group 11C on the outer petals changing to Yellow Group 11A in the center of the flower. The reverse sides of the petals are Yellow Group 11C on the outer petals changing to Yellow Group 11A in the center of the flower. The base of the petals has a small, 3/16"×3/16", bright Yellow Group 3B half-moon at the point of attachement. The major color on the upper sides is Yellow Group 11A.

*Variegations.*—Occasional greenish-white streak on the guard petals.

*Discoloration.*—At the end of the first day: No change. At the end of the third day: No change. There is a gradual fading on the plant. By day eight or nine, the entire flower is Yellow Group 11C.

*Fragrance.*—Slight. Character: Slight scent of anise.

Petals:

*Texture.*—Thick, leathery.

*Shape.*—Round.

*Form.*—Tips slightly recurved, edges slightly quilled.

*Arrangement.*—Imbricated. Petaloids in the center are few.

*Persistance.*—Petals drop off cleanly before drying.

*Lastingness.*—On the plant: Long (about 9–10 days). As a cut flower: Very long (16 to 18 days).

Reproductive parts:

*Anthers.*—Size: Medium. Quantity: Many. Color: Yellow. Arrangement: Regular around styles.

*Filaments.*—Color: Yellow.

*Pollen.*—Color: Gold-yellow.

*Styles.*—Color: Reddish.

*Stigmas.*—Color: Greenish-white.

Plant:

*Form.*—Bush.

*Growth.*—Very vigorous; upright; branching. Mature plant, after six months of growing in the greenhouse, is 5–5½ feet in height and 3½ feet in width.

Foliage: Number of leaflets on normal mid-stem leaves: Five.

*Size.*—Large (6½ inches×4¾ inches wide).

*Quantity.*—Abundant.

*Color.*—New Foilage: Upper side and lower sides: Greyed-Purple Group 184B with the upper surface rapidly turning green, the lower surface retaining the greyed-purple color for several days before turning green. Old foliage: Upper side: Green Group 139A. Lower side: Green Group 137C.

Leaflets:

*Shape.*—Pointed oval.

*Texture.*—Leathery. Surface: Matte.

*Edge.*—Serrated.

*Serration.*—Single, small.

*Petiole rachis.*—Color: Greyed-Purple Group 184C.

*Petiole underside.*—Smooth.

*Stipules.*—Medium (⅝"), serrated, bearded.

*Disease resistance.*—Resistant to mildew under normal growing conditions in a greenhouse. Not tested for resistance to blackspot and rust.

Wood:

*New wood.*—Color: Greyed-Purple Group 184C, but very quickly turing green. Bark: Smooth.

*Old wood.*—Color: Yellow-Green Group 146B. Bark: Smooth.

Prickles:

*Quantity.*—On main canes from base: Few. On laterals from main canes: Few.

*Form.*—Short, hooked slightly downward.

*Color when young.*—Greyed-Purple Group 183B.

*Color when mature.*—Greyed-Orange Group 177D.

Small Prickles:

*Quantity.*—On main stalks: None. On laterals: None.

I claim:

1. A new and distinct variety of rose plant of the floribunda class, as herein shown and described, characterized particularly by its yellow flower color; high flower production; excellent vase life; good shipping qualities; and very vigorous growth habit.

* * * * *

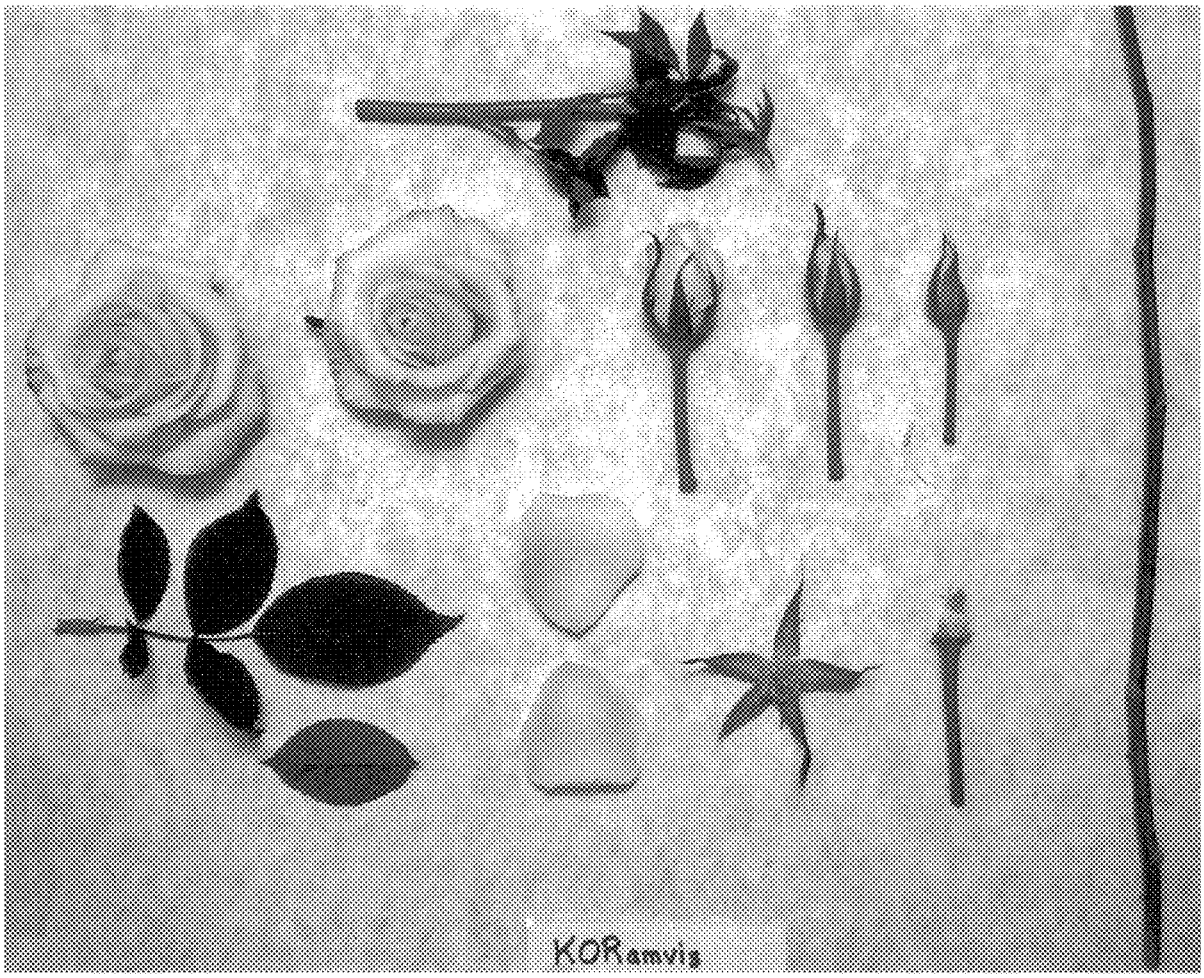
KORamvis